United States Patent
Kraft

(10) Patent No.: US 7,022,664 B2
(45) Date of Patent: Apr. 4, 2006

(54) 1,2 SUBSTITUTED 2,3-DIHYDRO-1H-5,9 DIOXACYCLOHEPTA[F]INDDEN-7-ONES AND 7-SUBSTITUTED BENZO[B][1,4]DIOXEPIN-3-ONES

(75) Inventor: Philip Kraft, Dübendorf (CH)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 10/424,612

(22) Filed: Apr. 28, 2003

(65) Prior Publication Data

US 2003/0207788 A1 Nov. 6, 2003

Related U.S. Application Data

(63) Continuation of application No. 09/816,631, filed on Mar. 23, 2001, now abandoned.

(30) Foreign Application Priority Data

Mar. 23, 2000 (CH) ..................... 0557/00

(51) Int. Cl.
*A61K 7/46* (2006.01)

(52) U.S. Cl. .................. 512/12; 512/25; 549/330; 549/331; 549/346; 549/347; 549/348; 549/349; 549/350; 549/354; 568/308; 568/325; 568/326; 568/329; 568/330

(58) Field of Classification Search .................. 512/12, 512/25; 549/330, 331, 346, 347, 348, 349, 549/350, 354; 568/308, 325, 326, 329, 330
See application file for complete search history.

(56) References Cited

U.S. PATENT DOCUMENTS 3,517,031 A 6/1970 Beereboo et al. ........... 260/333
5,990,076 A * 11/1999 Gaudin et al. ................. 512/1

FOREIGN PATENT DOCUMENTS

EP 0 902 024 A1 3/1999

OTHER PUBLICATIONS

European Search Report for EP 01105987dated Jul. 26, 2001.

* cited by examiner

*Primary Examiner*—Monique T. Cole
(74) *Attorney, Agent, or Firm*—Norris McLaughlin & Marcus PA

(57) ABSTRACT

The invention relates to 1,2-substituted 2,3-dihydro-1H-5,9-dioxacyclohepta[f]inden-7-ones and 7-substituted benzo[b][1,4]dioxepin-3-ones and to the use of these compounds in fragrance compositions.

21 Claims, No Drawings

1,2 SUBSTITUTED 2,3-DIHYDRO-1H-5,9 DIOXACYCLOHEPTA[F]INDDEN-7-ONES AND 7-SUBSTITUTED BENZO[B][1,4]DIOXEPIN-3-ONES

This application is continuation of U.S. patent application Ser. No. 09/816,631, filed Mar. 23, 2001, which is now abandoned.

FIELD OF THE INVENTION

The invention relates to 1,2-substituted 2,3-dihydro-1H-5,9-dioxacyclohepta[f]inden-7-ones and 7-substituted benzo[b][1,4]dioxepin-3-ones and to the use of these compounds in fragrance compositions.

BACKGROUND OF THE INVENTION

With the launch of an unusual marine women's fragrance, a new trend began to be established in perfumery at the beginning of the 1990s, which was continued in numerous similar marine fragrance creations and peaked in very successful feminine perfumes in 1996 and 1997. However, as soon as 1991 a successful marine men's fragrance also appeared on the market and in 1997 a bodycare series having an extremely marine effect. Virtually all of these marine fragrances are based on 7-methylbenzo[b][1,4]dioxepin-3-one (Calon 1951®). This key compound is described in Beereboom, et al. U.S. Pat. No. 3,647,479 ("Beereboom") together with derivatives which bear methyl, ethyl, propyl and butyl groups in the 7 position. Published patent EP 0 902 024 A1 describes the compound 7-propylbenzo[b][1,4]dioxepin-3-one and its use in perfumery. This compound comes under the general formula of Beereboom and has a similar odor to the abovementioned methyl derivative. To date, no further compounds of similar marine odor are known in perfumery.

SUMMARY OF THE INVENTION

Accordingly, it would be advantageous to provide novel compounds with a marine odor for use in perfumery.

One embodiment of the present invention is a compound of the general formula I:

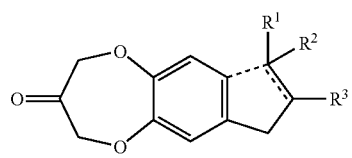

I wherein
$R^1$=H, $CH_3$, $CH_2CH_3$, $CH_2CH_2CH_3$, $CH(CH_3)_2$, $CH_2CH_2CH_2CH_3$,
$R^2$=H, or $CH_3$, and
$R^3$=H, $CH_3$, or $CH_2CH_3$, and the dashed line may be a double bond or a ring closure to form an indane ring system where, in the case of a double bond $R^1=R^2=H$, and in all other cases, the total number of carbon atoms of all residues is given by $C_8 > R^1+R^2+R^3 > C_1$.

A further embodiment of the present invention is a fragrance composition containing at least one compound according to formula I:

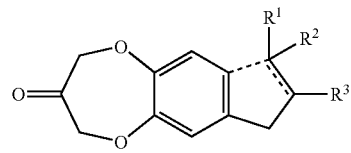

I wherein
$R^1$ is H, $CH_3$, $CH_2CH_3$, $CH_2CH_2CH_3$, $CH(CH_3)_2$, $CH_2CH_2CH_2CH_3$;
$R^2$ is H, or $CH_3$; and
$R^3$ is H, $CH_3$, or $CH_2CH_3$, and the dashed line is a double bond or a ring closure forming an indane ring system where, in the case of a double bond $R^1=R^2=H$, and in all other cases, the total number of carbon atoms of all residues in formula I is given by $C_8 > R^1+R^2+R^3 > C_1$.

Another embodiment of the present invention is a method for providing a fragrance by applying to a substrate a fragrance composition containing at least one compound according to formula I:

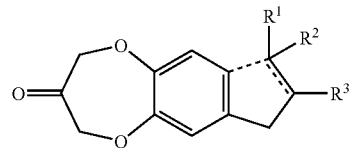

I wherein
$R^1$ is H, $CH_3$, $CH_2CH_3$, $CH_2CH_2CH_3$, $CH(CH_3)_2$, $CH_2CH_2CH_2CH_3$;
$R^2$ is H, or $CH_3$; and
$R^3$ is H, $CH_3$, or $CH_2CH_3$, and the dashed line is a double bond or a ring closure forming an indane ring system where, in the case of a double bond $R^1=R^2=H$, and in all other cases, the total number of carbon atoms of all residues in formula I is given by $C_8 > R^1+R^2+R^3 > C_1$.

DETAILED DESCRIPTION OF THE INVENTION

Surprisingly, it has now been found that compounds outside of the general formula of Beereboom also have marine odor properties, with additional completely unexpected, novel, and interesting properties. These compounds are summarized in the general formula I:

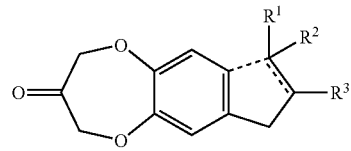

I where $R^1$=H, $CH_3$, $CH_2CH_3$, $CH_2CH_2CH_3$, $CH(CH_3)_2$, or $CH_2CH_2CH_2CH_3$, $R^2$=H, or $CH_3$, and $R^3$=H, $CH_3$, or $CH_2CH_3$, and the dashed line is an optional double bond or an optional ring closure to form the indane ring system, where in the case of a double bond $R^1=R^2$=H, and in all other cases the total number of carbon atoms of all residues is given by $C_8 > R^1 + R^2 + R^3 > C_1$.

In the case of the indane ring system, $R^1$ or $R^2$ is preferably $CH_3$.

The general formula I thus encompasses compounds 1–11:

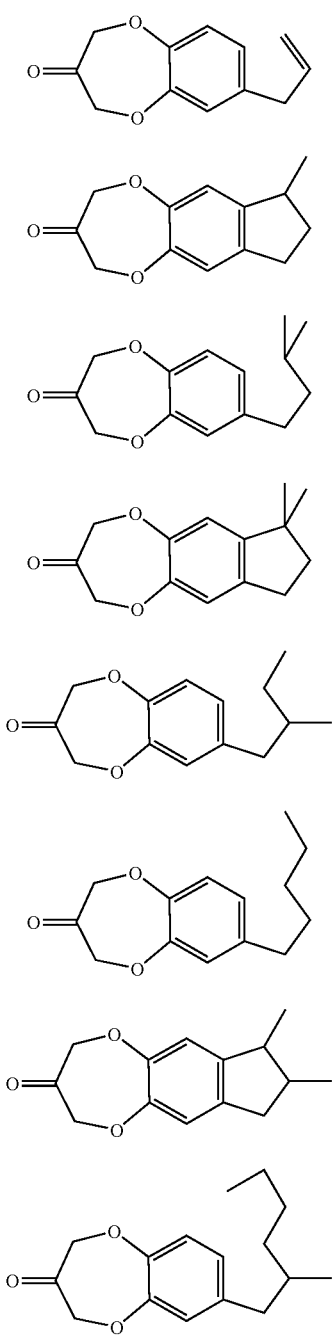

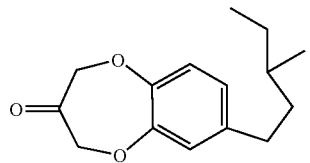

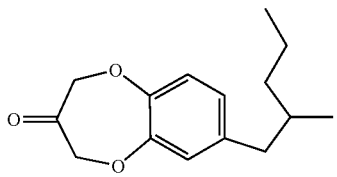

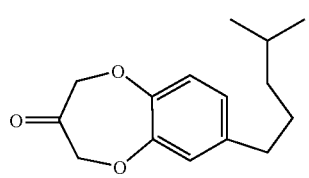

The compounds of the general formula I generally have a fresh, marine fragrance, generally with predominantly aldehydic, floral characters and are therefore particularly suitable for building up fresh, marine and aquatic effects, in particular, for instance, for modern marine Fougere perfumes and floral-aquatic women's fragrances. Those which are of particular interest for perfumes are harmonious blends of compound 1 with Tropional®, Melonal®, or Floralozon®. However, the use is neither restricted to these harmonious blends nor to specific fragrances, classes of substances or fragrance odors. Examples of further classes of substances which harmonize well include:

| | |
|---|---|
| Essential oils and extracts, e.g. | bergamot oil, grapefruit oil, jasmine absolue, mandarin oil, patchouli oil, vetiver oil, ylang-ylang oil, lemon oil. |
| Alcohols, ethers, acetals, e.g. | Acetal E ®, citronellol, dihydromyrcenol, Ebanol ®, eugenol, Florol ®, geraniol, Helional ®, cis-hex-3-enol, Mayol ®, 2-phenylethyl alcohol, Sandalor ®, Spirambren ®. |
| Aldehydes and ketones, e.g. | Adoxal ®, Bourgeonal ®, Cyclohexal ®, damascone, damascenone, Florhydral ®, Hedion ®, Iralia ®, Iso E Super ®, lauryl aldehyde, Lilial ®, methyl ionone, 2-methylundecanal, Myralden ®, undecanal, Vertofix ®. |
| Esters and lactones, e.g. | allyl amyl glycolate, benzyl salicylate, Cyclogalbanat ®, gamma-decalactone, Gardenol ®, geranyl acetate, cis-hex-3-enyl acetate, linalyl acetate, gamma-undecalactone, Verdox ®. |
| Macrocycles, polycycles, heterocycles, e.g. | Ambroxan ®, Cashmeran ®, Galaxolid ®, Habanolid ®, Thibetolid ®. |

The compounds of the present invention may be incorporated into fragrance compositions, which may be applied to various substrates, such as skin, hair, and articles of clothing, etc.

The following examples are provided to further illustrate the compounds of the present invention. These examples are illustrative only and are not intended to limit the scope of the invention in any way.

EXAMPLES

Example 1

7-allylbenzo[b][1,4]dioxepin-3-one (1)

A solution of 354 ml (2.30 mmol) of eugenol and 292 g (6.89 mol) of lithium chloride in 3.7 l of N,N-dimethylformamide was refluxed for a total of 44 hours (h), and, after 4 h, 22 h and 29 h, a further 292 g (6.89 mol) of lithium chloride were added each time. After cooling, 2 l of toluene were added and the resultant precipitate was filtered off with suction and extracted with toluene. The organic extracts were combined and concentrated on a rotary evaporator. After flash chromatography (ether/pentane, 1:1, $R_f$=0.37) on silica gel, 173 g (50%) of 4-allylcatechol were obtained.

12.8 g (225 mmol) of 95% pure sodium methoxide were introduced into a solution of 16.8 g (112 mmol) of 4-allylcatechol in 250 ml of methanol, with stirring, followed by 21 ml (225 mmol) of methyl bromoacetate. After refluxing for 8 h, a further 21 ml (225 mmol) of methyl bromoacetate were added, and, after a further 4 h of heating, a further 12.8 g (225 mmol) of sodium methoxide and a further 21 ml (225 mmol) of methyl bromoacetate. After a further 4 h under reflux, the mixture was worked up by adding 500 ml of ether and filtering off the precipitate formed. The filtrate was concentrated on a rotary evaporator and taken up in ether/water/saturated ammonium chloride solution (1:1:1). The organic phase was separated off, and the aqueous phase was extracted three times, each time with 200 ml of ether. The combined organic phases were dried over sodium sulfate and concentrated to dryness on a rotary evaporator. After flash chromatography (ether/pentane, 1:1, $R_f$=0.35) on silica gel, 21.4 g (65%) of methyl 4-allyl-2-(ethoxycarbonylmethoxy)phenoxyacetate were obtained.

A solution of 69.0 g (234 mmol) of methyl 4-allyl-2-(ethoxycarbonylmethoxy)phenoxyacetate was added dropwise in the course of 2.5 h to a suspension of 12.0 g (500 mmol) of sodium hydride in 500 ml of tetrahydrofuran. The reaction mixture was then refluxed for 20 h and, after cooling, poured into 1.5 l of ice water. The resultant mixture was acidified to pH 2 with 2N hydrochloric acid and extracted three times, each time with 2 l of ether. The combined ether extracts were dried over sodium sulfate, freed from solvent on a rotary evaporator and taken up into 400 ml of ethanol. 400 ml of 2N hydrochloric acid were added and the mixture was refluxed for 20 h. The mixture was then poured into 1.5 l of ice water, the product was extracted four times, each time with 1.5 l of ether, and the combined ether extracts were washed with 1 l of water and 100 ml of saturated sodium chloride solution. After drying over sodium sulfate, concentration on a rotary evaporator and flash chromatography. (pentane/ether, 4:1, $R_f$=0.37) on silica gel, 20.0 g (42%) of 7-allylbenzo[b][1,4]dioxepin-3-one (1) were obtained as a colorless liquid.

Odor: linear, very intensive marine-floral odor with nuances of ozone, watermelons and fatty aldehydes.—IR (film): ν=1502/1581/1436/1639 cm$^{-1}$ (ν C=C, Ar), 1742 cm$^{-1}$ (ν C=O), 1267/1305 cm$^{-1}$ (ν ring), 1051 cm$^{-1}$ (ν C—O—C).—$^1$H-NMR (CDCl$_3$): δ=3.30 (d, J=6.8 Hz, 2H, 1'-H$_2$), 4.68 (d, J=7.2 Hz, 2-, 4-H$_2$) 5.05–5.10 (m, 2H, 3'-H$_2$), 5.92 (m$_c$, 1H, 2'-H), 6.77–6.93 (m, 3H, 6-, 8-, 9-H).—$^{13}$C-NMR (CDCl$_3$): δ=39.15 (t, C-1'), 75.41/75.63 (2t, C-2,-4), 116.00 (t, C-3'), 120.67/120.73 (2d, C-6,-9), 123.73 (d, C-8), 135.94 (s, C-7), 136.88 (d, C-2'), 146.46 (s, C-9a), 148.00 (s, C-5a), 204.61 (s, C-3).—MS (EI): m/z (%)=91 (97) [C$_7$H$_7^+$], 120 (25) [C$_7$H$_4$O$_2^+$], 161 (13) [M$^+$-C$_2$H$_3$O], 175 (6) [M$^+$-CHO], 204 (100) [M$^+$].

Example 2

1-methyl-2,3-dihydro-1H-5,9-dioxacyclohepta[f]inden-7-one (2)

A mixture of 19.1 ml (150 mmol) of veratrol and 19.2 ml (225 mmol) of vinylacetic acid in 230 g of 83% polyphosphoric acid was stirred for 15 h at 60° C. and then poured into 500 ml of ice water. After 30 minutes (min) of stirring, the product was extracted three times, each time with 200 ml of ether. The combined organic phases were washed twice, each time with 100 ml of 2N NaOH, once with 100 ml of water and once with 50 ml of saturated sodium chloride solution, dried over sodium sulfate and freed from solvent on a rotary evaporator. After recrystallizing the residue (in AcOEt/pentane), 22.8 g (74%) of 5,6-dimethoxy-3-methylindan-1-one were obtained.

To a suspension of 53.3 g (815 mmol) of zinc dust in 74 ml of water were added 4 ml of concentrated hydrochloric acid. The supernatant was decanted off after stirring for 30 min, and to the residue were added, with ice cooling, 42 ml of water and then, dropwise, 55 ml of concentrated hydrochloric acid. 28.0 g (136 mmol) of 5,6-dimethoxy-3-methylindan-1-one dissolved in 53 ml of toluene were added and the mixture was refluxed for 3 days (d), in the course of which, after 48 h, a further 55 ml of concentrated hydrochloric acid were added. After cooling, the reaction mixture was poured into 200 ml of water and the product was extracted twice in 300 ml of ether. The combined extracts were washed with 100 ml of water and 25 ml of saturated sodium chloride solution, dried over sodium sulfate and concentrated on a rotary evaporator. After flash chromatography (pentane/ether, 9:1, $R_f$=0.23) on silica gel, 19.6 g (75%) of 5,6-dimethoxy-1-methylindane were obtained.

Over 90 min at room temperature, 27.5 ml (202 mmol) of iodotrimethylsilane were added dropwise with stirring to a solution of 19.4 g (101 mmol) of 5,6-dimethoxy-1-methylindane in 150 ml of acetonitrile. The mixture was stirred for a further 2.5 d at room temperature, in the course of which, after 48 h, again 10 ml (73.5 mmol) of iodotrimethylsilane were added. The reaction mixture was then poured into 500 ml of water and the product was extracted twice, each time with 200 ml of ether. The combined extracts were washed with 100 ml of 40% sodium hydrogen sulfite solution, 100 ml of water and 50 ml of saturated sodium chloride solution, dried over sodium sulfate and concentrated on a rotary evaporator. After flash chromatography (pentane/ether, 2:1, $R_f$=0.28) on silica gel, 15.5 g (93%) of 1-methylindane-5,6-diol were obtained.

A suspension of 25.7 g (186 mmol) of potassium carbonate were heated to reflux with stirring. At this temperature, over the course of 5 h, a mixture of 15.3 g (93.2 mmol) of 1-methylindane-5,6-diol and 11.6 g (92.8 mmol) of 3-chloro-2-chloromethylprop-1-ene dissolved in 50 ml of dioxane was added dropwise. When addition was complete, the mixture was stirred for a further 1 h under reflux and the inorganic solids precipitated out were filtered off with suction after cooling the reaction mixture. The solids were washed with acetone and the combined organic phases freed from solvent on a rotary evaporator. After flash chromatography (pentane/ether, 19:1, $R_f$=0.66) on silica gel, 7.3 g (36%) of 1-methyl-7-methylene-2,3,7,8-tetrahydro-1H,6H-5,9-dioxacyclohepta[f]indene were obtained.

6.6 g (30.5 mmol) of 1-methyl-7-methylene-2,3,7,8-tetrahydro-1H,6H-dioxacyclohepta[f]indene were dissolved in a mixture of 140 ml of acetonitrile, 140 ml of water and 90 ml of carbon tetrachloride. 6.50 g (30.5 mmol) of sodium periodate were added at room temperature with stirring, with the temperature falling to 15° C. After stirring for 30 min, 0.3 g (1.5 mmol, 5 mol %) of ruthenium (III) chloride hydrate were then added, with the temperature increasing back to 30° C. The mixture was stirred for 48 h at room temperature, in the course of which, after 6 h, a further 6.50 g (30.5 mmol) of sodium periodate and 0.3 g (1.5 mmol, 5 mol %) of ruthenium (III) chloride hydrate were added. The reaction mixture was then poured into 500 ml of water and the product was extracted three times, each time with 200 ml of dichloromethane. The combined organic extracts were washed with 200 ml of 20% sodium hydrogen sulfite solution and 200 ml of water and dried over sodium sulfate. After removing the solvent on a rotary evaporator and flash chromatography (pentane/ether, 4:1, $R_f$=0.32) on silica gel, 3.3 g (50%) of 1-methyl-2,3-dihydro-1H-5,9-dioxacyclohepta[f]inden-7-one (2) were obtained as colorless crystals of m.p. 79–80° C.

Odor: Linear, very intensive marine odor with strongly floral aspects.—IR (film): ν=1323/1280/1256/1351 cm$^{-1}$ (n ring), 1735 cm$^{-1}$ (ν C=O), 1041 cm$^{-1}$ (ν C—O—C sym), 1482/1439/1577 cm$^{-1}$ (ν C=C, Ar), 1155 cm$^{-1}$ (ν C—O—C asym).—$^1$H-NMR (CDCl$_3$): δ=1.24 (d, J=7.0 Hz, 3H, 1-Me), 1.60 (qd, J=12.4, 8.7 Hz, 1H, 2-H$_b$), 2.30 (tdd, J=12.4, 7.7, 3.9 Hz, 1H, 2-H$_a$), 2.74 (ddd, J=15.7, 8.7, 7.7 Hz, 1H, 3-H$_b$), 2.82 (ddd, J=15.7, 8.7, 3.9 Hz, 1H, 3-H$_a$), 3.10 (br. sext, J=7.0 Hz, 1H, 1-H), 4.66 (d, J=1.6 Hz, 4H, 6-,8-H$_2$), 6.80 (s, 1H, 4-H), 6.83 (s, 1H, 10-H).—$^{13}$C-NMR (CDCl$_3$): δ=19.78 (q, 1-Me), 30.70 (t, C-2), 35.13 (t, C-3), 38.88 (d, C-1), 75.49/75.53 (2t, C-6,-8), 115.15/116.17 (2d, C-4,-10), 139.19 (s, C-10a), 144.39 (s, C-3a), 146.82/146.97 (2s, C-4a, 9a), 205.03 (s, C-7).—MS (EI): m/z (%)=91 (97) [C$_7$H$_7$$^+$], 103 (20) [C$_8$H$_7$$^+$], 115 (13) [C$_8$H$_{19}$$^+$], 175 (14) [M$^+$-CH$_3$—CO], 203 (100) M$^+$-CH$_3$], 218 (57) [M$^+$].

The compounds of the general formula I listed in the examples below were synthesized according to the process of Example 2 by reaction of veratrol with the corresponding unsaturated and saturated carboxylic acids. Therefore, of these, only the odor descriptions and the spectroscopic data are listed.

Example 3

7-(3-methylbutyl)benzo[b][1,4]dioxepin-3-one (3)

Odor: Very intensive and diffuse, linear, marine odor with nuances of Adoxal® (2,6,10-trimethylundec-9-en-1-al).—IR (film): ν=1502/1435/1581/1467 cm$^{-1}$ (ν C=C, Ar), 1265/1304/1201 cm$^{-1}$ (ν ring), 1050 cm$^{-1}$ (ν C—O—C sym), 1740 cm$^{-1}$ (ν C=O),—$^1$H-NMR (CDCl$_3$): δ=0.92 (d, J=6.4 Hz, 6H, 3'-Me$_2$), 1.46/1.47 (2dd, J=8.0, 6.8 Hz, 2H, 2'-H$_2$), 1.57 (nonett, J=6.8 Hz, 1H, 3'-H), 2.52 (t, J= 8.0 Hz, 2H, 1'-H$_2$), 4.68 (d, J=9.2 Hz, 4H, 2-, 4-H$_2$), 6.77 (dd, J=8.2, 2.4 Hz, 1H, 8-H), 6.82 (d, J=2.4 Hz, 1H, 6-H), 6.90 (d, J=8.4 Hz, 1H, 9-H).—$^{13}$C-NMR (CDCl$_3$): δ=22.36 (2q, 3'-Me$_2$), 27.43 (d, C-3'), 32.69 (t, C-1'), 40.53 (t, C-2'), 75.35/75.63 (2t, C-2,-4), 120.27/120.50 (d, C-6,-9), 123.45 (d, C-8), 138.99 (s, C-7), 146.00/147.86 (2s, C-5a,-9a), 204.71 (s, C-3).—MS (EI): m/z (%)=77 (26) [C$_6$H$_6$$^+$], 135 (12) [M$^+$-C$_4$H$_9$—C$_2$H$_2$O], 149 (21) [M$^+$-C$_4$H$_9$—CO], 177 (100) [M$^+$-C$_4$H$_9$], 191 (7) [M$^+$-C$_3$H$_7$], 234 (52) [M$^+$].

Example 4

1,1-dimethyl-2,3-dihydro-1H-5,9-dioxacyclohepta[f]inden-7-one (4)

Odor: Marine-aldehyde-like, floral-rosy odor with nuances of citronelloxyacetaldehyde [(3,7-dimethyl-6-octenyl)oxyacetaldehyde].—IR (film): ν=1322/1253/1281/1350 cm$^{-1}$ (ν ring), 1040/1067 cm$^{-1}$ (ν C—O—C), 1484/1438 cm$^{-1}$ (ν C=C, Ar), 1736 cm$^{-1}$ (ν C=O). $^1$H-NMR (CDCl$_3$): δ=1.22 (s, 6H, 1-Me$_2$), 1.92 (t, J=7.2 Hz, 2H, 2-H$_2$), 2.79 (t, J=7.2 Hz, 2H, 3-H$_2$), 4.67 (d, J=2.8 Hz, 4H, 6-, 8-H$_2$), 6.75 (s, 1H, 4-H), 6.81 (s, 1H, 10-H).—$^{13}$C-NMR (CDCl$_3$): δ=28.43 (2q, 1-Me$_2$), 29.29 (t, C-3), 41.68 (t, C-2), 43.61 (s, C-1), 75.47/75.51 (2t, C-6,-8), 113.99 (d, C-10), 116.31 (d, C-4), 138.98 (s, C-3a), 146.83/147.22 (2s, C-4a, -9a), 148.30 (s, C-10a), 205.06 (s, C-7).—MS (EI): m/z (%)=133 (33) [C$_9$H$_9$O$^+$], 145 (6) [C$_{11}$H$_{13}$$^+$], 161 (7) [M$^+$—CH$_3$—2CO], 189 (2) [M$^+$-CH$_3$—CO], 217 (100) [M$^+$-CH$_3$], 232 (30) [M$^+$].

Example 5

7-(2-methylbutyl)benzo[b][1,4]dioxepin-3-one (5)

Odor: Intensive, marine-floral odor. IR (film): ν=1501/1434/1460/1580 cm$^{-1}$ (ν C=C, Ar), 1265/1302/1201 cm$^{-1}$ (ν ring), 1050 cm$^{-1}$ (ν C—O—C), 1740 cm$^{-1}$ (ν C=O).—$^1$H-NMR (CDCl$_3$): δ=0.84 (d, J=6.4 Hz, 3H, 2'-Me), 0.90 (t, J=7.5 Hz, 3H, 4'-H$_2$), 1.16 (m$_c$, 1H, 3'-H$_b$), 1.39 (m1$_c$, 1H, 3'-H$_a$), 160 (m$_c$, 1H, 2'-H), 2.28 (dd, J=11.6, 8.0 Hz, 1H, 1'-H$_a$), 2.53 (dd, J=11.6, 6.0 Hz, 1H, 1'-H$_b$), 4.69 (d, J=8.4 Hz, 4H, 2-, 4-H$_2$), 6.74 (dd, J=8.0, 2.0 Hz, 1H, 8-H), 6.78 (d, J=2.0 Hz, 1H, 6-H), 6.90 (d, J=8.0 Hz, 1H, 9-H).—$^{13}$C-NMR (CDCl$_3$): δ=11.32 (q, C-4'), 18.75 (q, 2'-Me), 28.95 (t, C-3'), 36.42 (d, C-2'), 42.22 (t, C-1'), 75.36/75.64 (2t, C-2,-4), 120.30/121.03 (2d, C-6,-9), 124.27 (d, C-8), 137.62 (s, C-7), 146.06/147.70 (2s, C-5a,-9a), 204.74 (s, C-3),—MS (EI): m/z (%)=77 (11) [C$_8$H$_5$$^+$], 91 (7) [C$_7$H$_7$$^+$], 135 (5) [M$^+$-C$_4$H$_9$—C$_2$H$_2$O], 149 (4) [M$^+$-C$_4$H$_9$—CO], 177 (100) [M$^+$-C$_4$H$_9$], 191 (2) [M$^+$-C$_3$H$_7$], 205 (1) [M$^+$-C$_2$H$_5$], 219 (1) [M$^+$-CH$_3$], 234 (26) [M$^+$].

Example 6

7-Pentylbenzo[b][1,4]dioxepin-3-one (6)

Odor: Marine, floral odor with aldehydic nuances.—IR (film): ν=1502/1435/1580 cm$^{-1}$ (ν C=C, Ar), 1265/1304/1201 cm$^{-1}$ (ν ring), 1050 cm$^{-1}$ (ν C—O—C), 1740 cm$^{-1}$ (ν C=O).—$^1$H-NMR (CDCl$_3$): δ=0.89 (t, J=7.0 Hz, 3H, 5'-H$_2$), 1.28–1.35 (m, 4H, 3'-, 4'-H$_2$), 1.59 (br. quint, J=7.6 Hz, 2H, 2'-H$_2$), 2.51 (t, J=7.8 Hz, 2H, 1'-H$_2$), 4.69 (d, J=9.6 Hz, 4H, 2-, 4-H$_2$), 6.77 (dd, J=8.0, 2.0 Hz, 1H, 8-H), 6.81 (d, J=2.0 Hz, 1H, 6-H), 6.90 (d, J=8.0 Hz, 1H, 9-H).—$^{13}$C-NMR (CDCl$_3$): δ=13.88 (q, C-5'), 22.38 (t, C-4'), 30.90/31.26 (t, C-2', -3'), 34.84 (t, C-1'), 75.35/75.64 (2t, C-2,-4), 120.31/120.47 (2d, C-6,-9), 123.51 (d, C-8), 138.85 (s, C-7), 146.03/147.83 (2s, C-5a,-9a), 204.72 (s, C-3-).—MS (EI): m/z (%)=77 (18) [C$_6$H$_5$$^+$], 91 (10) [C$_7$H$_7$$^+$], 135 (9) [M$^+$ $C_4H_9$—$C_2H_2O$], 149 (22) [$M^+$-$C_4H_9$—CO], 177 (100) [$M^+$-$C_4H_9$], 191 (8) [$M^+$-$C_3H_7$], 205 (1) [$M^+$-$C_2H_5$], 234 (42) [$M^+$].

Example 7

(E/Z)-1,2-dimethyl-2,3-dihydro-1H-5,9-dioxacyclohepta[f]inden-7-one (7)

Odor: Mixed odor of walnuts, *Trigonella foenumgraecum*, seawater and moss.—IR (film): ν=1736 cm$^{-1}$ (ν C=O), 1324/1263/1289/1352 cm$^{-1}$ (ν ring), 1484/1439 cm$^{-1}$ (ν C=C, Ar), 1042 cm$^{-1}$ (ν C—O—C sym), 1159 cm$^{-1}$ (ν C—O—C asym).—$^1$H-NMR (CDCl$_3$): δ=0.95/1.08/1.17/1.24 (4d, J=7.0 Hz, 6H, 1-, 2-Me), 1.91–2.02 (m, 1H, 2-H), 2.41 (dd, J=15.0, 9.6 Hz)/2.49 (dd, J=15.0, 6.4 Hz)/2.55 (dd, J=14.0, 6.8 Hz)/2.59 (dd, J=14.0, 7.2 Hz) [2H, 3-H$_2$], 2.89 (td, J=15.7, 7.2 Hz)/3.06 (quint, J=7.2 Hz) [1H, 1-H], 4.66 (d, J=1.6 Hz, 4H 4-, 8-H$_2$), 6.76–6.80 (m, 2H, 4-, 10-H).—$^{13}$C-NMR (CDCl$_3$): δ=14.50/15.00/17.54/18.31 (4q, 1,-2-Me), 38.64/39.38 (2t, C-3), 38.24/41.83/44.41/46.18 (4d, C-1,-2), 75.49/75.50/75.53/75.54 (4d, C-6,-8) 115.11/115.56/116.06/116.39 (4d, C-4,-10), 138.26/138.43 (2s, C-3a), 144.22/144.37 (2s, C-10a), 146.73/146.79/146.91/146.95 (4s, C-4a,-9a), 205.03/205.10 (2s,C-7).—MS (EI): m/z (%)=77 (13)/91(19)/105(20)/133(20)/161(7)/175(4) [$C_nH_{2n7}^+$], 189 (18) [$M^+$-$CH_3$—CO], 203 (1) [$M^+$-$C_2H_5$], 217 (100) [$M^+$-$CH_3$], 232 (70) [$M^+$].

Example 8

7-Hexylbenzo[b][1,4]dioxepin-3-one (8)

Odor: Marine, aquatic.—IR (film): ν=1502/1435/1580 cm$^{-1}$ (ν C=C, Ar), 1265/1304/1201 cm$^{-1}$ (ν ring), 1051 cm$^{-1}$ (ν C—O—C), 1741 cm$^{-1}$ (ν C=O).—$^1$H-NMR (CDCl$_3$): δ=0.88 (t, J=6.8 Hz, 3H, 6'-H$_2$), 1.27–1.35 (m, 6H, 3'-H$_2$-5'-H$_2$), 1.57 (br. quint, J=8.0 Hz, 2H, 2'-H$_2$), 2.51 (t, J=7.8 Hz, 2H, 1'-H$_2$), 4.68 (d, J=8.0 Hz, 4H, 2-, 4-H$_2$), 6.77 (dd, J=8.0, 4.0 Hz, 1H, 8-H), 6.81 (d, J=4.0 Hz, 1H, 6-H), 6.90 (d, J=8.0 Hz, 1H, 9-H).—$^{13}$C-NMR (CDCl$_3$): δ=13.96 (q, C-6'), 22.46 (t, C-5'), 28.77 (t, C-3'), 31.19/31.56 (2t,C-2',-4'), 34.89 (t, C-1'), 75.35/75.63 (2t, C-2,-4), 120.31/120.47 (2d, C-6,-9), 123.50 (d, C-8), 138.85 (s, C-7), 146.03/147.83 (2s, C-5a,-9a), 204.73 (s, C-3).—MS (EI): m/z (%)=77 (16) [$C_8H_6^+$], 91 (9) [$C_7H_7^+$], 135 (9) [$M^+$-$C_5H_{11}$—$C_2H_2O$], 149 (21) [$M^+$-$C_5H_{11}$—CO], 177 (100) [$M^+$-$C_5H_{11}$], 191 (2) [$M^+$-$C_4H_9$], 205 (3) [$M^+$-$C_3H_7$], 248 (43) [$M^+$].

Example 9

7-(3-methylpentyl)benzo[b][1,4]dioxepin-3-one (9)

Odor: Marine, animalic, civet-like, floral-aldehyde odor, also somewhat reminiscent of citronelloxyacetaldehyde ([3,7-dimethyl-6-octenyl]oxy-acetaldehyde).—IR (film): ν=1502/1435/1460/1580 cm$^{-1}$ (ν C=C, Ar), 1265/1304/1202 cm$^{-1}$ (ν ring), 1051 cm$^{-1}$ (ν C—O—C), 1741 cm$^{-1}$ (ν C=O).—$^1$H-NMR (CDCl$_3$): δ=0.87 (t, J=7.2 Hz, 3H, 5'-H$_3$), 0.91 (d, J=6.4 Hz, 3H, 3'-Me), 1.18 (m$_{c1}$ 1H, $^{2'}$-H$_b$), 1.34–1.43 (m, 3H, 2'-H$_a$, 4'-H$_2$), 1.56–1.62 (m, 1H, 3'-H), 2.48 (ddd, J=14.0, 10.0, 6.4 Hz, 1H, 1'-H$_a$), 2.56 (ddd, J=14.0, 10.4, 5.2 Hz, 1H, 1'-H$_b$), 4.67 (d, J=2.4 Hz, 4H, 2-,4-H$_2$), 6.78 (dd, J=8.2, 2.4 Hz, 1H, 8-H), 6.82 (d, J=2.0 Hz, 1H, 6-H), 6.90 (d, J=8.4 Hz, 1H, 9-H).—$^{13}$C-NMR (CDCl$_3$): δ=11.14 (q, C-5'), 18.93 (q, 3'-Me), 29.18 (t, C-4'), 32.42 (t, C-1'), 33.84 (t, C-3'), 38.23 (t, C-2'), 22.38 (t, C-4'), 30.90/31.26 (2t, C-2', -3'), 75.35/75.64 (2t, C-2,-4), 120.27/ 120.51 (2d, C-6,-9), 123.45 (d, C-8), 139.11 (s, C-7), 146.00/147.86 (2s, C-5a,-9a), 204.72 (s, C-3).—MS (EI): m/z (%)=77 (21) [$C_8H_5^+$], 92 (14) [$C_7H_8^+$], 135 (11) [$M^+$-$C_5H_{11}$—$C_2H_2O$], 149 (16) [$M^+$-$C_5H_{11}$—CO], 177 (100) [$M^+$-$C_5H_{11}$], 191 (4) [$M^+$-$C_4H_9$], 205 (7) [$M^+$-$C_3H_7$], 248 (45) [$M^+$].

Example 10

7-(2-Methylpentyl)benzo[b][1,4]dioxepin-3-one (10)

Odor: Marine, floral-aldehyde odor.—IR (film): ν=1501/1434/1460/1580 cm$^{-1}$ (ν C=C, Ar), 1265/1303/1201 cm$^{-1}$ (ν ring), 1049 cm$^{-1}$ (ν C—O—C), 1740 cm$^{-1}$ (ν C=O).—$^1$H-NMR (CDCl$_3$): δ=0.83 (d, 3H, 2'-Me), 0.88 (t, J=7.0 Hz, 3H, 5'-H$_3$), 1.11–1.40 (m, 4H, 3'-,4'-H$_2$), 1.68 (m$_{c1}$ 1H, 2'-H), 2.26 (dd, J=13.6, 8.4 Hz, 1H, 1'-H$_b$), 2.54 (dd, J=13.6, 6.0 Hz, 1H, 1'-H$_a$), 4.69 (d, J=8.4 Hz, 4H, 2-,4-H$_2$), 6.73 (dd, J=8.0, 2.0 Hz, 1H, 8-H), 6.78 (d, J=2.0 Hz, 1H, 6-H), 6.89 (d, J=8.0 Hz, 1H, 9-H).—$^{13}$C-NMR (CDCl$_3$): δ=14.15 (q, C-5'), 19.17 (q, 2'-Me), 20.02 (t, C-4'), 34.50 (d, C-2'), 38.77 (t, C-3'), 42.61 (t, C-1'), 75.36/75.63 (2t, C-2,-4) 120.30/121.04 (2d, C-6,-9), 124.28 (d, C-8), 137.61 (s, C-7), 146.05/147.70 (2s, C-5a,-9a), 204.77 (s, C-3).—MS (EI): m/z (%)=77 (9) [$C_6H_5^+$], 91 (6) [$C_7H_7^+$], 135 (5) [$M^+$-$C_5H_{11}$—$C_2H_2O$], 149 (3) [$M^+$-$C_5H_{11}$—CO], 177 (100) [$M^+$-$C_5H_{11}$], 205 (2) [$M^+$-$C_3H_7$], 248 (21) [$M^+$].

Example 11

7-(4-methylpentyl)benzo[b][1,4]dioxepin-3-on (11)

Odor: Marine, floral-aldehyde odor.—IR (film): ν=1502/1418/1466/1580 cm$^{-1}$ (ν C=C, Ar), 1265/1304/1201 cm$^{-1}$ (ν ring), 1050 cm$^{-1}$ (ν C—O—C), 1741 cm$^{-1}$ (ν C=O).—$^1$H-NMR (CDCl$_3$): δ=0.88 (2d, J=6.4 Hz, 6H, 4'-Me$_2$), 1.18–1.24 (m, 2H, 3'-H$_2$), 1.53–1.61 (m, 4H, 2'-H$_2$, 4'-H), 2.50 (t, J=7.8 Hz, 2H, 1'-H$_2$), 4.69 (d, J=8.0 Hz, 4H, 2-, 4-H$_2$), 6.78 (dd, J=8.0, 4.0 Hz, 1H, 8-H), 6.82 (d, J=4.0 Hz, 1H, 6-H), 6.90 (d, J=8.0 Hz, 1H, 9-H).—$^{13}$C-NMR (CDCl$_3$): δ=22.44 (2q, 4'-Me$_2$), 27.74 (d, C-4'), 29.07 (t, C-2'), 35.14 (t, C-1'), 38.39 (t, C-3'), 75.35/75.63 (2t, C-2,-4), 120.30/120.48 (2d, C-6,-9), 123.50 (d, C-8), 138.86 (s, C-7), 146.03/147.83 (2s, C-5a,-9a), 204.76 (s, C-3).—MS (EI): m/z (%)=77 (13) [$C_6H_5$+], 91 (8) [$C_7H_7^+$], 135 (7) [$M^+$-$C_5H_{11}$—$C_2H_2O$], 149 (16) [$M^+$-$C_5H_{11}$—CO], 177 (100) [$M^+$-$C_5H_{11}$], 191 (1) [$M^+$-$C_4H_9$], 205 (3) [$M^+$-$C_3H_7$], 248 (38) [$M^+$].

The compounds 7-(2-ethylbutyl)benzo[b][1,4]dioxepin-3-one and 7-heptylbenzo[b][1,4]dioxapin-3-one also have the faceted marine odor typical of this class of compound and are therefore suitable, as are the abovementioned compounds, for preparing harmonious fragrance blends having marine notes. In this regard, the abovementioned compounds 1 and 3 are particularly outstanding, as shown by the examples below.

Example 12

| No. | Compound/constituent | Floral-marine-fruity women's fragrance containing compound 1 Contents by weight in parts per thousand |
|---|---|---|
| 1. | Citronellol extra | 30 |
| 2. | Cyclohexal | 150 |

-continued

Floral-marine-fruity women's fragrance containing compound 1

| No. | Compound/constituent | Contents by weight in parts per thousand |
|---|---|---|
| 3. | Damascone 10% in DPG | 2 |
| 4. | gamma-Decalactone | 2 |
| 5. | beta-Dihydroionone | 55 |
| 6. | DPG (dipropylene glycol) | 76 |
| 7. | Eugenol, pure | 35 |
| 8. | Galaxolid 50 BB | 275 |
| 9. | Hedion | 110 |
| 10. | Iso E Super | 145 |
| 11. | Jasmolactone (Firmenich) 1 percent strength in DPG | 25 |
| 12. | Linalool, synthetic | 30 |
| 13 | Compound 1, 10% in DPG | 65 |
|   |   | 1000 |

The composition produces a feminine-sensual, transparent, modern perfume with a rosy-floral, fresh jasmine-like head and floral-fruity heart note with spicy aspects on a musky-wooden base.

Compound 1 gives the composition its marine aspects, and gives it its radiance and richness in character. It transforms the traditional floral fragrance into a modern-transparent, trend perfume. In comparison with the compound 7-methylbenzo[b][1.4]dioxepin-3-one, that is to say Calon 1951® mentioned at the outset, compound 1 is much more intense and, at the same dosage, is accompanied by a much stronger marine impression without transition into fishy or salty, as is the case with Calon 1951® at the high dosage here. The compound 1 is much more floral than Calon 1951® and therefore harmonizes much better with the floral elements of the composition. It develops the floral-aquatic accord, while remaining transparent.

Example 13

Feminine floral-marine perfume containing compound 3

| No. | Compound/constituent | Contents by weight in parts per thousand |
|---|---|---|
| 1. | Algenon PB | 100 |
| 2. | Benzyl salicylate | 110 |
| 3. | Bergamot oil, Italian | 50 |
| 4. | Boisambren forte | 10 |
| 5. | Cyclohexal | 12 |
| 6. | Dihydromyrcenol | 35 |
| 7. | DPG (dipropylene glycol) | 358 |
| 8. | Eugenol, pure | 10 |
| 9. | Fixolid | 10 |
| 10. | Galaxolid 50 PHT | 65 |
| 11. | Georgywood | 25 |
| 12. | Hedion | 20 |
| 13. | Linalool, synthetic | 10 |
| 14. | Linalyl acetate, synthetic | 30 |
| 15. | Sandela | 25 |
| 16. | Tropional | 75 |
| 17. | Vertofix Coeur | 35 |
| 18. | Compound 3, 10% in DPG | 20 |
|   |   | 1000 |

Compound 3 enhances the fresh, marine impression of the composition. It combines harmoniously with the hesperidic topnote, emphasizes the floral heart note and finally blends in the base with woody and musk-like notes to give a character harmonious composition. Compound 3 provides volume, radiance and body to the composition. It gives the impression of a fresh sea breeze. Compared with Calon 1951® (see Example 12), compound 3 is much more intense, but nevertheless does not have a heavy or suppressive effect on the other constituents of the composition. In contrast, compound 3 brings the perfume more radiance, diffusivity and volume than Calon 1951®.

The invention being thus described, it will be obvious that the same may be varied in many ways. Such variations are not to be regarded as a departure from the spirit and scope of the invention and all such modifications are intended to be included within the scope of the following claims.

What is claimed is:

1. A compound of formula (Ia):

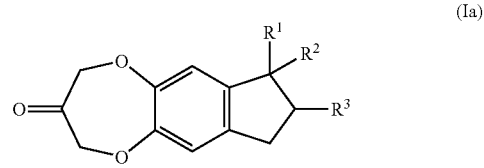

(Ia)

wherein for formula (Ia):

$R^1$ is H, $CH_3$, $CH_2CH_3$, $CH_2CH_2CH_3$, $CH(CH_3)_2$, $CH_2CH_2CH_2CH_3$;

$R^2$ is H, or $CH_3$; and $R^3$ is H, $CH_3$, or $CH_2CH_3$, wherein the total number of carbon atoms of all residues in formula (Ia) is given by $C8>R^1+R^2+R^3>C1$.

2. A compound according to claim 1 wherein, $R^1$ or $R^2=CH_3$.

3. The compound according to claim 1 selected from the group consisting of:

7-allylbenzo[b][1,4]dioxepin-3-one, 1-methyl-2,3-dihydro-1H-5,9-dioxacyclohepta[f]inden-7-one, 1,1-dimethyl-2,3-dihydro-1H-5,9-dioxacyclohepta[f]inden-7-one, 1,2-dimethyl-2,3-dihydro-1H-5,9-dioxacyclohepta[f]inden-7-one.

4. A compound according to claim 3 selected from the group consisting of:

7-allylbenzo[b][1,4]dioxepin-3-one, 1-methyl-2,3-dihydro-1H-5,9-dioxacyclohepta[f]inden-7-one, 1,1-dimethyl-2,3-dihydro-1H-5,9-dioxacyclohepta[f]inden-7-one, 1,2-dimethyl-2,3-dihydro-1H-5,9-dioxacyclohepta[f]inden-7-one.

5. A compound according to claim 4 which is 7-allylbenzo[b][1,4]dioxepin-3-one.

6. A fragrance composition comprising at least one compound of formula (Ia) or formula (Ib):

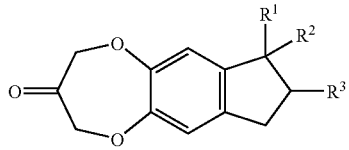
(Ia)

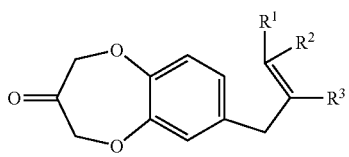
(Ib)

wherein
for formula (Ia):
R¹ is H, CH₃, CH₂CH₃, CH₂CH₂CH₃, CH(CH₃)₂, CH₂CH₂CH₂CH₃;
R² is H, or CH₃; and
R³ is H, CH₃, or CH₂CH₃, wherein the total number of carbon atoms of all residues in formula (Ia) is given by C8>R1+R2+R3>C1; and
for formula (Ib):
R¹ and R² is H; and
R³ is H, CH₃, or CH₂CH₃.

7. A fragrance composition according to claim 6 wherein the compound of formula Ia and Ib is selected from the group consisting of:
7-allylbenzo[b][1,4]dioxepin-3-one,
1-methyl-2,3-dihydro-1H-5,9-dioxacycl-ohepta[f]inden-7-one,
1,1-dimethyl-2,3-dihydro-1H-5,9-dioxacyclohepta[f]inden-7-one,
1,2-dimethyl-2,3-dihydro-1H-5,9-dioxacyclohepta[f]inden-7-one, and mixtures thereof.

8. A fragrance composition according to claim 7 wherein the compound of formula Ia and formula Ib is selected from the group consisting of:
7-allylbenzo[b][1,4]dioxepin-3-one,
1-methyl-2,3-dihydro-1H-5,9-dioxacycl-ohepta[f]inden-7-one,
1,1-dimethyl-2,3-dihydro-1H-5,9-dioxacyclohepta[f]inden-7-one,
1,2-dimethyl-2,3-dihydro-1H-5,9-dioxacyclohepta[f]inden-7-one, and mixtures thereof.

9. A fragrance composition according to claim 8 wherein the compound of formula I is 7-allylbenzo[b][1,4]dioxepin-3-one.

10. A method for providing a fragrance comprising: applying to a substrate a fragrance composition comprising at least one compound of formula (Ia) or formula (Ib):

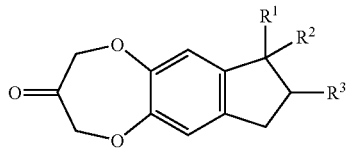
(Ia)

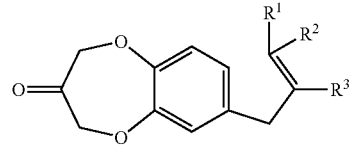
(Ib)

wherein
for formula (Ia):
R¹ is H, CH₃, CH₂CH₃, CH₂CH₂CH₃, CH(CH₃)₂, CH₂CH₂CH₂CH₃;
R² is H, or CH₃; and
R³ is H, CH₃, or CH₂CH₃, wherein the total number of carbon of all residues in formula (Ia) is given by C8>R1+R2+R3>C1; and
for formula (Ib):
R¹ and R² is H; and
R³ is H, CH₃, or CH₂CH₃.

11. A method according to claim 10 wherein the compound of formula I is selected from the group consisting of
7-allylbenzo[b][1,4]dioxepin-3-one,
1-methyl-2,3-dihydro-1H-5,9-dioxacyclohepta[f]inden-7-one,
1,1-dimethyl-2,3-dihydro-1H-5,9-dioxacyclohepta[f]inden-7-one,
1,2-dimethyl-2,3-dihydro-1H-5,9-dioxacyclohepta[f]inden-7-one, and mixtures thereof.

12. A method according to claim 11 wherein the compound of formula I is selected from the group consisting of
7-allylbenzo[b][1,4]dioxepin-3-one,
1-methyl-2,3-dihydro-1H-5, 9-dioxacyclohepta[f]inden-7-one,
1,1-dimethyl-2,3-dihydro-1H-5,9-dioxacyclohepta[f]inden-7-one,
1,2-dimethyl-2,3-dihydro-1H-5,9-dioxacyclohepta[f]inden-7-one, and mixtures thereof.

13. A method according to claim 12 wherein the compound of formula I is selected 7-allylbenzo[b][1,4]dioxepin-3-one.

14. A compound as claimed in claim 4 which is 1-methyl-2,3-dihydro-1H-5,9-dioxacyclohepta[f]inden-7-one.

15. A fragrance composition according to claim 8 wherein the compound is 1-methyl-2,3-dihydro-1H-5,9-dioxacyclohepta[f]inden-7-one.

16. A method according to claim 12 wherein the compound is 1-methyl-2,3-dihydro-1H-5,9-dioxacyclohepta[f]inden-7-one.

17. A compound of formula (Ib):

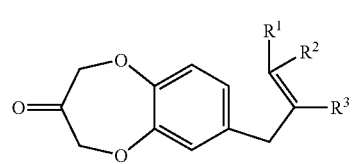
(Ib)

wherein
R¹ and R² is H; and
R³ is H, CH₃, or CH₂CH₃.

18. The compound according to claim 17 selected from the group consisting of 7-allylbenzo[b][1,4]dioxepin-3-one,
1-methyl-2,3-dihydro-1H-5,9-dioxacyclohepta[f]inden-7-one,
1,1-dimethyl-2,3-dihydro-1H-5,9-dioxacyclohepta[f]inden-7-one,
1,2-dimethyl-2,3-dihydro-1H-5,9-dioxacyclohepta[f]inden-7-one.

19. A compound as claimed in claim 18 selected from the group consisting of 7-allylbenzo[b][1,4]dioxepin-3-one,
1-methyl-2,3-dihydro-1H-5,9-dioxacyclohepta[f]inden-7-one,
1,1-dimethyl-2,3-dihydro-1H-5,9-dioxacyclohepta[f]inden-7-one,
1,2-dimethyl-2,3-dihydro-1H-5,9-dioxacyclohepta[f]inden-7-one.

20. A compound according to claim 19 which is 7-allyl-benzo[b][1,4]dioxepin-3-one.

21. A compound as claimed in claim 19 which is 1-methyl-2,3-dihydro-1H-5,9-dioxacyclohepta[f]inden-7-one.

* * * * *